US012806363B2

(12) United States Patent
Llana García

(10) Patent No.: US 12,806,363 B2
(45) Date of Patent: Nov. 24, 2026

(54) BREATHING TREATMENT EQUIPMENT

(71) Applicant: BIOWAIR TOTAL SYSTEMS, S.L., Gijon (ES)

(72) Inventor: Pedro Luis Llana García, Gijon (ES)

(73) Assignee: BIOWAIR TOTAL SYSTEMS, S.L., Gijon (ES)

( * ) Notice: Subject to any disclaimer, the term of this patent is extended or adjusted under 35 U.S.C. 154(b) by 1058 days.

(21) Appl. No.: 17/780,329

(22) PCT Filed: Nov. 27, 2020

(86) PCT No.: PCT/ES2020/070744

§ 371 (c)(1),
(2) Date: May 26, 2022

(87) PCT Pub. No.: WO2021/105543

PCT Pub. Date: Jun. 3, 2021

(65) Prior Publication Data

US 2023/0019440 A1 Jan. 19, 2023

(30) Foreign Application Priority Data

Nov. 28, 2019 (EP) .................................... 19383056

(51) Int. Cl.
*F24F 8/10* (2021.01)
*A61L 9/014* (2006.01)
(Continued)

(52) U.S. Cl.
CPC .......... *A61M 16/105* (2013.01); *A61L 9/014* (2013.01); *A61L 9/205* (2013.01);
(Continued)

(58) Field of Classification Search
CPC ........... A61M 16/105; A61M 16/1055; A61M 16/0051; A61M 2206/11;
(Continued)

(56) References Cited

U.S. PATENT DOCUMENTS

| | | | |
|---|---|---|---|
| 3,724,172 A | 4/1973 | Wood | |
| 2011/0030560 A1 | 2/2011 | Bohlen et al. | |

(Continued)

FOREIGN PATENT DOCUMENTS

| | | | | |
|---|---|---|---|---|
| CN | 1985130 A | * | 6/2007 | ............... A61L 9/00 |
| CN | 201229034 Y | * | 4/2009 | |

(Continued)

OTHER PUBLICATIONS

CN-105571009-A Machine Translation (Year: 2025).*

(Continued)

*Primary Examiner* — Kendra D Carter
*Assistant Examiner* — Keira Eileen Callison
(74) *Attorney, Agent, or Firm* — Wenderoth, Lind & Ponack, L.L.P.

(57) ABSTRACT

A breathing treatment device includes a motorized air recirculation system, filters for air purification, an ultraviolet (UV) ray sterilizer, a plasma electrostimulator, an ejector of air in laminar flow with noise emission between 0 dB and 5 dB, a redirector of the laminar flow towards a head of a patient, a stabilizer, a multifilament diffuser, and at least one UV-C light-emitting diode (LED).

13 Claims, 7 Drawing Sheets

(51) Int. Cl.
*A61L 9/20* (2006.01)
*A61M 16/10* (2006.01)
*A61M 16/00* (2006.01)

(52) U.S. Cl.
CPC ...... *A61M 16/1055* (2013.01); *A61L 2209/12* (2013.01); *A61L 2209/14* (2013.01); *A61L 2209/22* (2013.01); *A61M 16/0051* (2013.01); *A61M 2206/11* (2013.01)

(58) Field of Classification Search
CPC .. A61M 2205/7509; A61M 2205/7518; A61M 2021/0027; A61M 16/0066; A61M 21/02; A61L 9/014; A61L 9/205; A61L 2209/12; A61L 2209/14; A61L 2209/22; A61L 9/20; A61L 9/22; F24F 8/10; F24F 8/158; F24F 8/22; F24F 8/30; F24F 2221/125; F24F 2221/17; F24F 13/081; F24F 2013/205; F24F 8/80
See application file for complete search history.

(56) References Cited

U.S. PATENT DOCUMENTS

| | | | | |
|---|---|---|---|---|
| 2014/0299406 A1* | 10/2014 | Librett | A61M 16/0858 181/224 |
| 2017/0072082 A1* | 3/2017 | Jurak | A61L 2/10 |
| 2018/0154297 A1* | 6/2018 | Maletich | F24F 8/10 |
| 2019/0059242 A1* | 2/2019 | Bogner | A01G 9/18 |

FOREIGN PATENT DOCUMENTS

| | | | | |
|---|---|---|---|---|
| CN | 105571009 | | 5/2016 | |
| CN | 105571009 A | * | 5/2016 | |
| CN | 105605695 | | 5/2016 | |
| CN | 206330269 U | * | 7/2017 | |
| CN | 107062452 | | 8/2017 | |
| CN | 207052429 U | * | 2/2018 | |
| CN | 108981007 A | * | 12/2018 | |
| CN | 110360660 A | * | 10/2019 | |
| EP | 3 021 808 | | 5/2016 | |
| KR | 20090061228 A | * | 6/2009 | B01D 39/00 |
| WO | WO-2005039659 A1 | * | 5/2005 | A61L 9/16 |
| WO | 2009/120166 | | 10/2009 | |
| WO | WO-2013117895 A1 | * | 8/2013 | F04D 25/08 |
| WO | WO-2014175809 A1 | * | 10/2014 | A47C 19/022 |
| WO | 2015/009344 | | 1/2015 | |
| WO | WO-2019132111 A1 | * | 7/2019 | F24F 11/39 |

OTHER PUBLICATIONS

CN-110360660-A Machine Translation with Labeled Paragraphs (Year: 2025).*
CN-110360660-A Machine Translation (Year: 2025).*
CN-206330269-U Machine Translation (Year: 2025).*
CN 206330269 U Machine Translation with labeled paragraphs (Year: 2025).*
CN-201229034-Y Machine Translation (Year: 2025).*
CN-207052429-U Machine translation with labeled paragraphs (Year: 2025).*
CN-207052429-U Machine translation (Year: 2025).*
WO-2019132111-A1 Machine Translation with labeled paragraphs (Year: 2025).*
WO-2019132111-A1 Machine Translation (Year: 2025).*
KR-20090061228-A Machine Translation with labeled paragraphs (Year: 2025).*
KR-20090061228-A Machine Translation (Year: 2025).*
CN-108981007-A Machine Translation (Year: 2025).*
CN-1985130-A machine translation (Year: 2025).*
International Search Report issued Apr. 8, 2021 in corresponding International Application No. PCT/ES2020/070744.
International Preliminary Report on Patentability issued Feb. 11, 2022 in corresponding International Application No. PCT/ES2020/070744.

* cited by examiner

16

BREATHING TREATMENT EQUIPMENT

OBJECT OF THE INVENTION

The object of the present invention is to provide a breathing treatment equipment or device that achieves cell regeneration for therapeutic purposes to be placed in the users resting enclosure, as well as a method for the treatment of breathing conditions by using said device.

BACKGROUND OF THE INVENTION

A number of studies demonstrate that longevity and health are associated with the length of the sequence of telomeres at the end of cellular DNA. The shorter it is, the more possibilities there are of problems in DNA replicates and therefore cell death or failure, which is directly associated with old age and health. The length of the sequence of telomeres is affected by three factors:

The hereditary (genetic and epigenetic, that is, DNA and its relationship with the environment) factor, the food (diet) factor and the environmental factor (pollution, viruses and bacteria, stress, rest). Therefore, there is a need for devices that can directly affect the environmental factor, that can prevent environmental pollutants, remove nanoparticles, viruses and bacteria, and which allow the body to naturally drain out contaminants, facilitating rest, increasing sleeping time and quality, and reducing stress. This is achieved by altering the intercellular environment, releasing it from biological, physical and chemical toxins. Facilitating oxygenation of the blood and cleaning of the circulatory system.

Therefore, a system is desired which does all that mentioned above, particularly cleaning and better oxygenating the blood by treating the patient while he/she sleeps. The present invention meets this demand.

DESCRIPTION OF THE INVENTION

The present invention refers to a cell regeneration equipment by means of a breathing treatment that facilitates the cleaning of the intercellular environment through a breathing treatment and a better general oxygenation of the organism, especially while the user or patient sleeps. This is achieved by air treatment 24 hours a day, 365 days a year of the room where the user sleeps and/or where he/she spends more hours with the cell regeneration and breathing treatment equipment according to the present invention:

Through the cell regeneration and breathing treatment equipment, it is possible to reduce the number of nanoparticles in the blood, also avoiding the entry of allergens associated with them and the sedimentation of particles in the blood vessels, as well as preventing the nanoparticles from reaching the intercellular matrix. Therefore, the use is mainly to improve the circulatory system, improve mitochondrial performance and increase the production of essential amino acids while the purifiers are designed above all for a specific use that alleviates allergy problems. The use of the device is more preventive, continuous and deeper, for the improvement of the whole organism.

Main Features and Main Advantages of the Cellular Regeneration and Breathing Treatment Equipment According to the Present Invention Filter System:

The cell regeneration and breathing treatment equipment according to the present invention by means of its filter system removes viruses, bacteria, molds, yeasts, gases, volatile organic compounds, formaldehydes and all kinds of contaminants that could potentially reach the blood of a user through the users breathing obtaining a totally clean space permanently. In such a way that the user achieves an ultra-healthy intensive breathing, especially while sleeping, thanks to the present invention, since the cell regeneration and air treatment equipment allows cleaning not only allergens, dust, mites, etc., from the air, but nanoparticles as well.

Operating Modes:

The cell regeneration and breathing treatment equipment according to the present invention has two overnight operating options:

1) a first mode in which the cell regeneration and breathing treatment equipment is 100% silent, or
2) a second mode in which the cell regeneration and breathing treatment equipment generates low-intensity white noise (three different levels) which, along with the permanently treated air, advantageously makes the user enjoy a deep and restorative sleep, increasing hours of rest, facilitating the nasal breathing, eliminating dryness, snoring, and in many cases preventing the use of sleep apnea masks. It has a function specifically defined to prevent insomnia. Therefore, as a result of the cell regeneration and breathing treatment equipment according to the present invention, complete rest is obtained while the user sleeps.

Cold or Hot Air Jet:

The cell regeneration and breathing treatment equipment according to the present invention allows sending to the patient immediately and in a targeted manner cool air or hot air, preventing colds since this is done with completely sterilized air, thus obtaining a thermal conditioning of the room without viruses or bacteria. It is ideal for sick people and people with immunodeficiencies. This reduces the need to open windows (contamination), using air conditioning, or using heaters which move around temperature-activated viruses and bacteria. To prevent insomnia, the thermal sensation must be kept between 18 and 24° C.

Removal of Allergens:

The cell regeneration and breathing treatment equipment removes allergens on both a macro level and on a level of transfer by association with nanoparticles, which is the cause of the increase in number and seriousness of allergies. Said removal must be carried out permanently, so the machine works 24 hours a day; this means that the body gradually decreases allergen levels in the entire body. This allows the patient to become more resistant to any type of allergies. In this way they no longer suffer respiratory attacks which make it difficult to oxygenate the blood and increase the heart rate. With improved blood oxygenation due to fewer respiratory attacks, the entire body will be more active, everything will work better, particularly those systems most related to microcirculation, such as the brain, the skin, the reproductive system, the immune system, etc.

Therefore, all this assures that, particularly while sleeping, the user breathes completely treated and sterilized air, allowing the body of the user to regenerate as it is free of contaminants, since it has been demonstrated that the environment inside the home is up to eight times more contaminated than outside the home and comprises pollutants released from walls, ceilings, fabrics, paints, varnishes, furniture, etc., create various irritations in the respiratory system which entail inflammations which complicate breathing, creating rhinitis, snoring, apneas, and in summary, a lack of rest. Furthermore, these contaminants are not filtered out by the lungs and go directly to the blood, transporting by contact any type of allergens to all the organs through the blood.

The cell regeneration and breathing treatment equipment according to the present invention reverses these effects of contaminants, assuring every night that the body regenerates, is purified, increasing blood oxygenation upon releasing hemoglobin from nanoparticles that reach the blood and occupy the position of oxygen molecules, preventing the transport of oxygen to the organs. This will mean that the entire body works better, particularly the purifying and immune system and microcirculation (all the internal organs internal, particularly the brain, the reproductive system, immune system, the skin, etc.). Furthermore, nanoparticles deposited in veins and arteries will be removed, since the entry of contaminants will be stopped and natural draining of the body will be facilitated while resting. The body will also enjoy the improvements throughout the rest of the day as a result of the better oxygen delivery to all the internal systems.

The size of the materials that are removed from the air can comprise up to a millimeter divided by 10,000 times, so it is not filtered by the lungs and directly reaches the blood. Therefore, the cell regeneration and respiratory treatment equipment according to the present invention comprises a permanent air recirculation system of up to 3 cycles per hour/24 hours a day of room air that is treated by filtering equipment comprising:

Parts of the equipment for cell regeneration and breathing treatment according to the present invention:

The cell regeneration and breathing air treatment equipment comprises a motor comprising a system of tubular blades and a tubular steel integral recirculation system which allows the passage of air repeatedly through:

A filter system or package comprising a washable pre-filter for coarse particles, a special blue antibacterial filter to keep the filter free from biological material, a HEPA 13 (High Efficiency Particulate Air) filter, and an activated carbon filter with catalytic platinum, which removes gases, formaldehydes, smells, etc.

Furthermore, the equipment comprises a stainless steel particle filter which allows obtaining a coarse filtration during extraction of the filter system when washing said filter system or during a considerable increase in air flow rate.

An ultraviolet ray sterilizer, breaking down the DNA of viruses and bacteria. The exposure of air to ultraviolet treatment by means of the ultraviolet ray sterilizer must be controlled certain hours a day, avoiding use thereof overnight so as not to be a nuisance for anyone who is sleeping or not to excessively sterilize the room.

A plasma electrostimulator changing the electric charge of the contaminating nanoparticles (which are virtually impossible to filter), so that they return to the environment with a charge contrary to the nanoparticles of air in the room, thus associating with the air nanoparticles because of their difference in electric charge and creating a larger particle that can indeed be filtered. The plasma electrostimulator must operate at calibrated intervals with air renewal so as not to change the charge of the entire room. These systems may be regulated by remote control from any mobile, will provide a log of the hours of use of each part of the equipment, and will allow the doctor or specialist to adjust the use to each patient remotely based on the log.

A deflector for the continuous laminar air flow which allows directing the laminar flow towards the face of the patient for optimal breathing.

Nanoparticle Control System and Laser Measuring Device:

The cell regeneration and breathing treatment equipment according to the present invention can operate in the room 24 hours a day and is beneficial for health, particularly while the user sleeps. This equipment must include control systems since each user has different behaviors and tolerances. For this reason, the cell regeneration and breathing treatment equipment includes means for remote control. All the controls for the treatment of that person may be customized.

The equipment will incorporate as standard a fully automatic operating system that comes with a standard pre-programming and incorporates a standard use of both filtration, and treatment speed, as well as programming of UV ray sterilizers and plasma electrostimulators such that the equipment is set only to the customs of the user. To that end, the equipment incorporates a multilevel air nanoparticle laser measuring device which measures three different values, nanoparticles of 1 micron, PM 2.5 and average PM from 2.5 to 10 microns. The combination of values of this type allows an automatic setting that is entirely based on the patient's BPR (Blood Pollution Risk), and is a permanent indicator that the user can see and has extremely precise values that allow being set to each home, each patient, and each lifestyle. To do all this, the equipment will also incorporate a system which detects when the patient goes to sleep (light-sensitive cell), such that the equipment transitions at that time to night mode, assuring its operation in absolute silence. Thus the patient can sleep without any type of nuisance, without any type of apnea mask, without any type of vibration, or noise, or light or nuisance of any type.

This control system also allows family members to have real information about the use or customs, sleeping hours, etc., of the user, if this is what the user wants.

Motor and Silicon Stabilizer:

Achieving the equipment working while the user sleeps without bothering said user, removing nanoparticles, is extremely difficult, since air must be passed at a high pressure but low speed through high-density HEPA air purification equipment and activated carbon air purification equipment which make noise as the air passes therethrough. To that end, another novelty will be used, said novelty being very special high-powered low-consumption motors working at low speeds and high pressures. This results in vibrations, and therefore nuisances. To that end, a unique vibration absorption system has been developed based on a high-density silicon stabilizer which, placed on the equipment, absorbs vibrations of this type, along with the body of the equipment which, for that purpose, has been made 100% from steel and silicon, thus creating a high-density module that eliminates vibrations and allows giving the equipment a service life of over 35 years. The unit of the present invention will accompany the user 24 hours, 365 days a year, for up to 50 years.

To act on the exogenous factors affecting the length of telomeres, the quality of sleep must be an indispensable part of the treatment. Better rest and suitable oxygenation will create the ideal state to avoid stress and make the body work better; the circulation, brain, breathing, musculature, the skin, the hair, and all the internal organs in general will optimally function. As a result, to achieve 100% silent equipment which at the same time removes nanoparticles and prevents noises, a system combining the motor and a tubular steel integral circulation system which allows continuous, uninterrupted use for 50 years has been designed.

The motor works at low speed, but generates enough pressure for the air to overcome high-density filters of any type. This, in turn, creates two types of noises: Whistling air and vibrations due to the power of the motor:

The first case (whistling) is avoided by setting the motor through electronics to an ultra-low speed, but with enough pressure to make the air pass through all the filters without making noise. This favors the removal of nanoparticles but requires much more time of use, which is why the equipment operates continuously.

Vibrations are created by centrifugal forces of the motor and the system of tubular blades. These vibrations are unavoidable, but a method for dissipating them against the high density of the steel body of the equipment has been invented. As this was not enough, a vibration dissipator has been added, which consists of a high-density silicon mass, fired at 1.250° C., which, because of its high weight and being attached to the body of the equipment, absorbs vibrations, preventing noises and nuisances for the user.

The arrangement of these motors and air moving systems must be in the horizontal position and at a specific height from the floor to assure that the best air in the room, i.e. the air that was just treated, reaches the lungs of the patient. However, this must be done without creating any nuisance or interrupting rest; therefore, at the air outlet, there is a framework of steel sheets which carry out two functions:

1) Atomizing the air such that the user does not perceive a bothersome stream while he/she sleeps.
2) Heating the steel sheets assuring that the treated air additionally has the desired temperature.

All this air will have previously passed through the ultraviolet ray sterilizer and through the plasma electro-stimulator. It is all remotely controlled in a completely automatic manner as a result of the WiFi communication system and the nanoparticle laser measurement system which allows immediately being set automatically according to the pollution both inside and outside the room.

Placement of the Equipment and Continuous Laminar Flow Deflector:

The equipment furthermore has a shape which means that it is to be located with respect to the height of the head of a patient at a height between 60-160 cm from the floor to be able to send the treated air directly to the patient's respiratory stream, creating a gentle sheet of air directed at the face of the user while he/she sleeps, but without causing any type of nuisance or requiring masks of any type. To that end, a continuous laminar flow has been developed which sends atomized air so gently and continuously that it is barely noticed (unlike the turbulent flow of purifiers, which is distributed everywhere and is a nuisance), thus the patient always breathes in the best air that may be in the room (as it exits the machine) and without nuisances of any type. The equipment thus has solid aluminum diffusers assuring the correct air direction, as well as deflectors in the upper part also made of solid aluminum. Furthermore, the equipment has laminar flow redirecting means, particularly a large-sized deflector slat, preferably made of aluminum, which allows diverting the continuous laminar flow towards the face of the patient for optimal breathing.

The equipment in its entirety is conceived for the patient to immediately receive the treated air. For this purpose it has the described shape, arrangement, and operation.

When a patient sleeps, even though the air is clean, the movement of the patient in bed and against the bedding means that the patient breathes in partially contaminated air due to the particles released by the sheets, by his/her own breathing, by that of his/her companion, or even by multiple substances (including mites) that may be in the pillow. The cell regeneration and breathing treatment equipment sends a pure laminar air flow which the patient will not notice since it is a low-intensity continuous laminar flow and that will carry any type of harmful substance away from the patient's breathing range, and will clean the surface of the patient's bed constantly.

The equipment provides considerable improvements to the quality of sleep, since it requires the patient to be truly relaxed for his/her body to optimally heal. To that end, it incorporates a special design especial in the upper part that imitates the sound box of a musical instrument. This allows transforming the vibrations characteristic of the motor into low-intensity white noise which is used in white function, 2 and 3 as an option for the relaxation while the patient sleeps. The combination of this low-intensity white noise together with the air completely treated 24 hours a day means that the rest and relaxation are deep and restorative. The patient may choose from absolute silence or three white noise intensities.

The equipment can be installed in the wall of an enclosure, but it incorporates a standard support system with or without wheels, which allows the patient to place it in the optimal position for the continuous laminar flow to reach his/her lungs while he/she sleeps, as well as to move it from one room to another depending on who needs it more for health issues.

Light-Sensitive Cell for Night Mode Activation:

To do all this, the equipment also incorporates a system which detects when the patient is ready to go to sleep (light-sensitive cell), such that the equipment at that time transitions to night mode, assuring its operation in absolute silence. Thus the patient can sleep without any type of nuisance, without any type of apnea mask, without any type of vibration, or noise, or light or nuisance of any type.

Design:

The cell regeneration and breathing treatment equipment is designed for use as a shelf and for complete integration in the wall of a house, such that the equipment is entirely integrated in the house, no longer being an obstacle in the house like conventional purifiers. Furthermore, its design allows any type of objects such as books, television sets, music equipment, decorations, etc., to be placed on it since they will not experience interference or vibrations.

The special shape of the equipment is particularly designed to output a film of treated air by means of a continuous laminar flow towards the face of the patient while he/she sleeps such that this said patient always enjoys the best treated air in the room. Furthermore, the equipment has a large-sized deflector slat which allows diverting the continuous laminar flow towards the face of the patient for optimal breathing.

It also has a support for use by athletes for the purpose of improving their performance while they train on a treadmill, exercise bike, or other forms of indoor training. Its use with support assures the correct usage height and orientation of the continuous laminar flow towards the patient. The equipment in its entirety is conceived for the patient to immediately receive the treated air. For this purpose it has the described shape, arrangement, and operation.

Use:

The use of the breathing treatment equipment is entirely different from that of a purifier, since it is not designed for isolated use, but rather for permanent use 24 hours a day. Although a normal purifier also removes fine particles, it is especially designed for isolated uses, giving priority to power or speed to rapidly remove allergens from the environment when necessary. The breathing treatment equipment according to the present invention is designed to be used permanently, working at a very low speed to increase the Brownian effect and thus particularly remove the finest nanoparticles.

This is a continuous low-speed operating process which allows the room in which the equipment is installed to always have an optimal nanoparticle count, and which furthermore directs the treated air towards the respiratory tract of the patient.

Particularly during nighttime use, the equipment enhances rest as a result of the insertion of low-intensity white noise. This deep rest is key to the use of the equipment, since only in that state will the recovery and drainage of the patient's entire body be promoted. For that effect and taking into account the fact that the ideal thermal sensation for rest is between 18 and 24° C., the equipment sends a fresh laminar air flow towards the user, as well as a hot air flow if needed since it incorporates a thermostat and a heat or cool air system.

Removal of Molds and Fungi:

The equipment is also used to remove molds and fungi from the house, since it combines the bactericidal task with the thermal function of preventing the house from dropping below 16% C. It thus prevents dampness and the proliferation of spores. Conventional purifiers are designed for the respiratory system and the equipment is furthermore designed for the circulatory system, relaxation and rest.

Materials:

Conventional purifiers are basically made of plastic, and after a short usage time turn yellow and age. The breathing treatment equipment comprises materials such as steel, aluminum and silicon, which are designed to operate for up to 50 years continuously, 24 hours a day. The equipment is for professional, medically prescribed use. Furthermore, in order to operate with those powerful, low-speed but high-pressure, low-consumption, steel motors, the equipment must incorporate a system for preventing vibrations. This is achieved as a result of the high-density silicon stabilizer designed to absorb vibrations and convert them into low-intensity white noise. Purifiers incorporate none of this.

Longevity:

Conventional air purifiers have a short service life, tend to deteriorate, make noise, turn yellow, age, and end up being an environmental problem, as they have to be recycled at a huge economic and ecological cost. The equipment does not age; all its components are interchangeable and 100% recyclable. The equipment has a useful life of 50 years, with what that means from the ecological point of view and from the user's point of view.

Arrangement in the House:

The equipment is designed to be placed at a height between 60-160 cm from the floor. In an alternative embodiment, the equipment also has wheel systems which allow it to be positioned at that height. It is thereby assured that the continuous laminar flow stream reaches the user at the height of his/her face while he/she sleeps, facilitating breathing and preventing the entry of particles that may cause irritations in the airways, making rest difficult. The equipment is designed to be strategically placed in the house to assure a stratum of air in perfect state, even in houses with high ceilings. They are also designed to create laminar flow streams running through the house at the height of the user such that the equipment of the present invention operates by communicating areas with one another, making the air flow from room to room. The equipment therefore has not only a local, isolated function, but rather when strategically placed by professionals, it assures treatment in the entire house for all the people living in it. That is, it is designed for a coordinated use.

Sound Warning System:

The equipment incorporates a sound warning system, particularly an alarm, in the event that pollution levels in the air increase at an alarming rate, which could represent a small fire while the person is sleeping or absent from the room, for example. This alarm will communicate via sound in the room and over the Internet to users authorized by the patient.

Data Acquisition System:

The equipment has a global data acquisition system which allows, by means of the use of artificial intelligence, being autopredictive, thus optimally adapting to the uses and customs of each patient, each house, and each town. All this data, subject to authorization by the client, allows emitting any type of statistic related to treatments, the lowering of medicines, including the curtailment of diseases, and of course control in the longevity of the users of the equipment, such that, the improvements in the quality and longevity of the life of patients can be unquestionably documented in the future. Additionally, the equipment incorporates a high-quality display which permanently reports the blood pollution risk level (instantaneous nanoparticle level), as well as the temperature of the room, the systems of the equipment in operation, a light-sensitive control system to adapt to the rest mode, etc.

Therefore, the equipment stands out because of its continuous ultra silent operation, the vibration absorption system for making it silent, the automatic and remote control system for medical monitoring. The system comprises maximum design strength (no plastics) to last for 50 years of continuous use; the equipment is arranged horizontally; and it is a low-consumption system since the equipment operates from only a consumption of 6 W/h, assuring insignificant electricity consumption. Furthermore, the white noise production system is designed for the relaxation, concentration and rest of the user.

Therefore, in a first aspect, the present invention relates to a breathing treatment device for therapeutic purposes for placement thereof in a patient resting enclosure, the device comprising a motor-powered air recirculation system, a set of air purification filters, an ultraviolet ray sterilizer and a plasma electrostimulator. The device is characterized in that it comprises laminar air flow ejection means, laminar air flow redirecting means for redirecting flow towards the head of the patient, a stabilizer and anchoring means to anchor the device to a wall.

In a preferred embodiment, the device is arranged at a height between 60-160 cm with respect to the floor of the enclosure. Additionally, the laminar air flow redirecting means for redirecting flow towards the face of the patient comprise an aluminum deflector.

In a preferred embodiment, the device comprises a diffuser interposed between the patient and the laminar flow. In another preferred embodiment, the device comprises a support system for arranging the device at a height between 60-160 cm with respect to the floor of the enclosure, preferably with wheels.

In a preferred embodiment, the device comprises wireless transmission means, preferably WiFi and/or Bluetooth and/or a LED display (16).

In a preferred embodiment, the device comprises a pre-filter, a blue antibacterial filter, a HEPA 13 filter and an activated carbon filter with catalytic platinum (10*d*). Furthermore, in another preferred embodiment, the device comprises a stainless steel filter (10*e*). In a preferred embodiment, the stabilizer comprises silicon and/or steel.

In a preferred embodiment, the device comprises a silent operating mode or a low-intensity white noise operating mode. Furthermore, in another preferred embodiment, the device comprises a multilevel nanoparticle laser measuring device and/or an audible alarm.

In another aspect, the invention relates to a method for the treatment of breathing conditions. The method comprises placement of the device at a height between 60-160 cm with respect to the floor of an enclosure and the application of a laminar air flow generated by said device above the head of a patient.

DESCRIPTION OF THE DRAWINGS

As a complement to the description being provided, and for the purpose of helping to make the features of the electric generator more readily understandable, according to a preferred example of a practical embodiment thereof, a set of drawings is attached as an integral part of said description, in which, with an illustrative and non-limiting nature, the following has been represented

PREFERRED EMBODIMENT OF THE INVENTION

Figure 1:
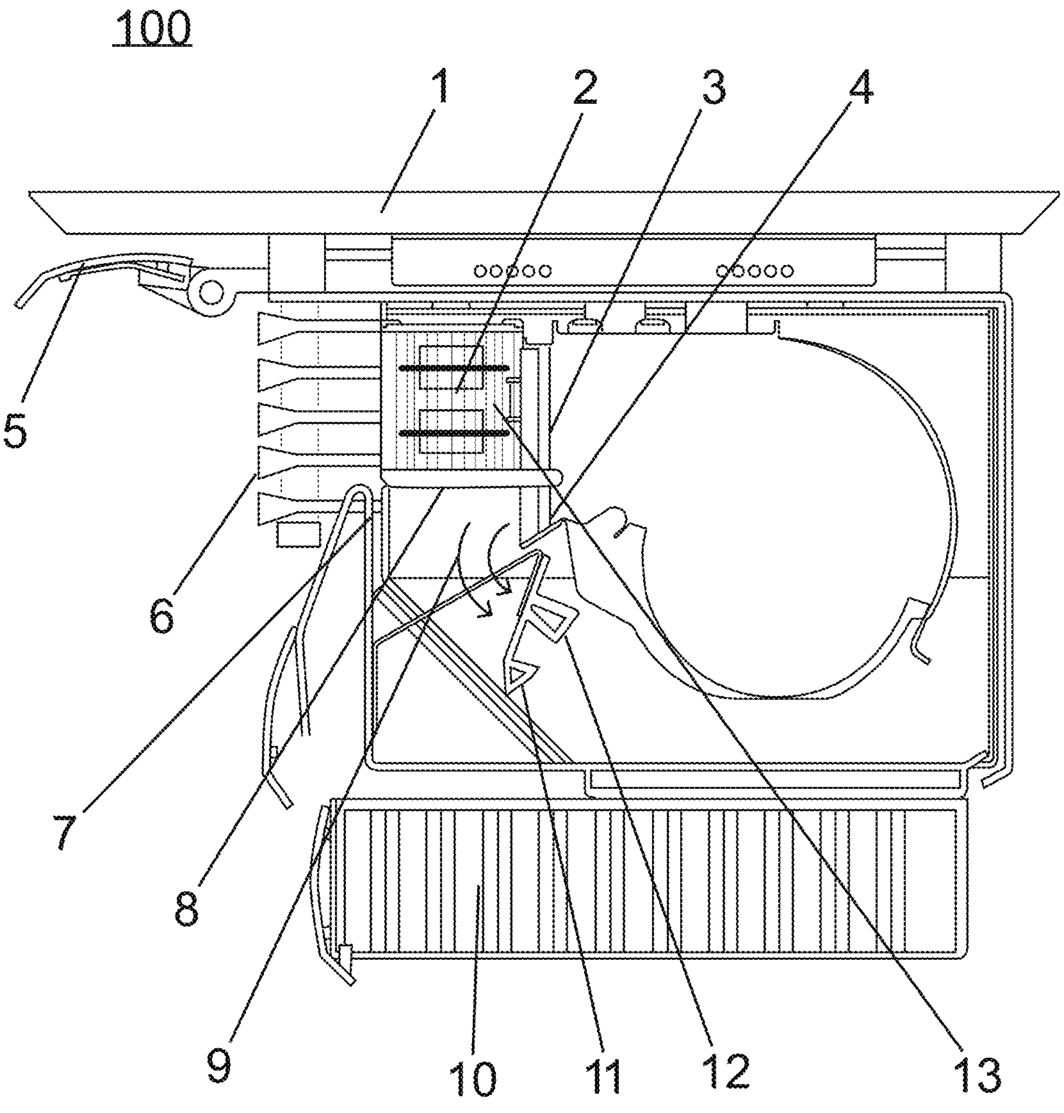
FIG. 1 shows the cell regeneration and breathing treatment equipment according to the present invention.

FIG. 1 shows a breathing treatment equipment (100) according to the present invention.

The cell regeneration and breathing treatment equipment (100) comprises:

- a silicon stabilizer (1) that prevents vibrations, a multifilament diffuser (2) preferably made of stainless steel where the air is subdivided into hundreds of vertical sheets dispersing and slowing down its passage, an ejection flow means (3) for the air ejection, a recirculation flow means (4) for recirculation of air inside the cell regeneration and breathing treatment equipment (100), an aluminum deflector (5), aluminum compression sheets (6) that slow down the laminar flow without creating noise, vibrations or turbulence, a deflector blade for recirculation (7), an air flow divider (8) comprising a micanita insulating protector, a recirculation channel (9), a multiple filter system (10), a set of UV-C LEDs (11), ionizers (12) and a resistivity system for thermal sterilization (13).

Breathing Sweep:

The cell regeneration and breathing treatment equipment (100) has a horizontal arrangement with a length between 50 and 120 cm that provides a laminar flow of treated air to create a breathing sweep. That is, a sheet of treated air, i.e. free of nanoparticles, viruses and bacteria, and which reaches the face of the patient before being contaminated in a path e.g. between 60 and 140 cm.

100% Silent:

The cell regeneration and breathing treatment equipment (100) is 100% silent. This is achieved by combining laminar flow, passing speed versus filter size (preferably filters (400/800×40×160) and tangential fans (400-800 mm) in parallel and horizontal arrangement, with DC levitation motors to avoid friction, electronically keeping the speed of air passing through the filters electronically ultra-low and eliminating all types of vibrations typical of the centrifugal forces exerted by a moving motor. These vibrations are absorbed by the high-density silicon stabilizer (1) placed on the upper part of the equipment for this purpose, which is connected perimetrically with the resonance box inside the equipment. With all this, between 0 and 5 Db is achieved in silent night mode, running at 550 Rpm.

The cell regeneration and breathing treatment equipment (100) comprises a high density silicon stabilizer (1) (2.3 gr/cm3) with a weight of 7.5 kg to absorb all types of vibrations avoiding noise and hum.

Imperceptible Laminar Flow:

The cell regeneration and breathing treatment equipment (100) emits an air flow so that the patient does not perceive it. A stream of air would prevent sleep, irritate the skin, and create eye and ear problems. For this, the cell regeneration and respiratory treatment equipment (100) comprises a stainless steel multifilament diffuser (2) in a vertical arrangement which, placed at the outlet of the air ejector, divides it into thousands of parts creating a sensation similar to that of the air through a tree. That is, the air is subdivided into hundreds of vertical sheets dispersing and slowing down its passage. The metal sheets of the multifilament diffuser (2) have a distance between them between 2 to 4 mm and comprise an arrangement such as e.g. vertical oblong rings or springs that prevent whistles or noises when passing air.

Subsequently, this air is redirected horizontally through compression plates (6) preferably made of aluminum and in the shape of a trumpet that, like channels, are arranged at the air outlet horizontally, further slowing down the laminar flow without creating noise or vibrations or turbulence. Thus, the air will reach the patient imperceptibly without turbulence.

In order for a user to sleep without being disturbed by air streams in the face, the combination of various factors that generate laminar flow and not turbulent flow is essential.

The cell regeneration and breathing treatment equipment (100) includes an extra-long horizontal tangential fan (400-800 mm), and a parallel filtering system of the same size (400/800×40 mm×160 mm), with a separation distance (chamber) between 25 and 40 mm.

The cell regeneration and breathing treatment equipment (100) comprises a DC direct current motor and electronics that reduce the revolutions of the ventilation system depending on the reading of nanoparticles in the air and the presence of light (night mode), working in four modes:

Silent mode: 550 Rpm,
White mode: 750 Rpm,
mode V2: 950 Rpm,
mode V3: 1200 Rpm,

In this way, the air is directed through the ejection area through the multifilament diffuser (2) preferably made of stainless steel where the air is subdivided into hundreds of vertical sheets dispersing and slowing it down, where the flow is broken and finally the air passes through aluminum compression plates (6) that slow down the laminar flow without creating noise, vibrations or turbulence and that direct it in a stable horizontal way, thus guaranteeing a continuous laminar flow (1930 Reynolds medium laminar flow).

UV-C Sterilization Optimization System

Figure 2:
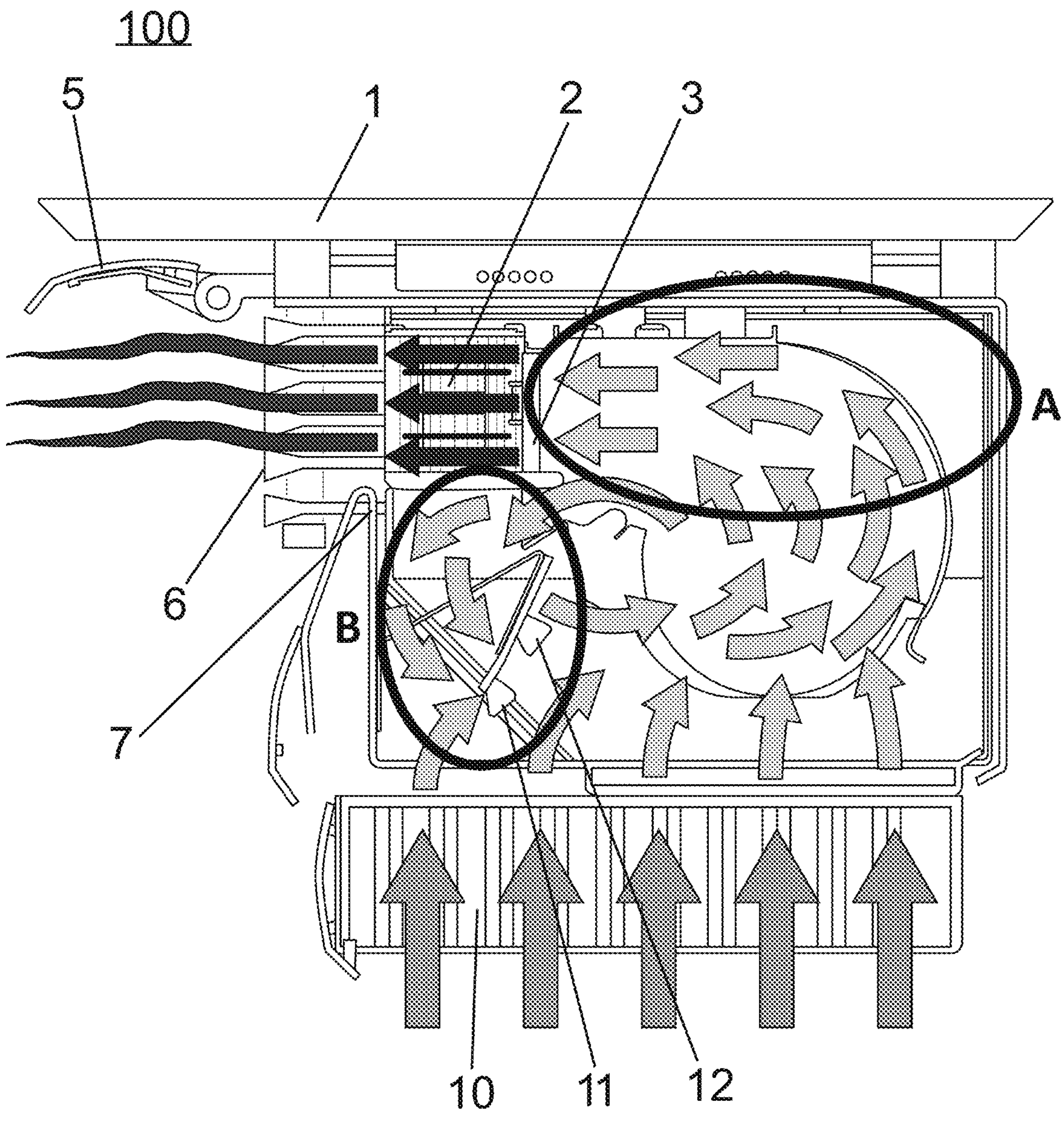
FIG. 2 shows the airflows of the breathing treatment equipment.

The cell regeneration and breathing treatment equipment (100) incorporates a UV-C LED sterilization system (11). The sterilizing effect on viruses and bacteria is proportional to the exposure time of the air flow to UV-C rays. To increase this exposure time, the cell regeneration and breathing treatment equipment (100) incorporates a dual channel ejection mode i.e. split flow with multiple cycles, as shown in FIG. 2, where a first flow A comprising between 70 and 85% of the air with PM particles "particulate matter" greater than 1 μm passes to the multifilament diffuser (2) and is expelled to the outside and where a second flow B comprising the remaining flow i.e. 15/30% PM particles smaller than 1 μm are recirculated into the cell regeneration and breathing treatment equipment (100), being exposed again to UV-C LEDs (11).

Thus, an air flow (A) is created that circulates on the outside of the tangential ventilation duct. This flow (A) drags the heaviest particles (PM greater than 1 μm) by centrifugal force, which will be ejected to the outside through the thermal sterilizer. An air flow (B) is created through the internal part of the rotor, through which the nanoparticles (PM less than 1 μm) pass, which will be sent back into the equipment for retreatment with UV-C, Ion and plasma ion. This is done because the deactivation of viral and bacterial DNA requires the longest possible exposure time. Said nanoparticles will move by centrifugal force towards flow (A), until they are ejected through the thermal sterilizer. In this way it is achieved that the air ejected to the outside does not transport biomass.

This cycle is constantly repeated so that the air is renewed by the centrifugal force of the tangential fan, so that throughout the day all the air in the room where the user or patient is located has passed at least e.g. 200 times per UV-C sterilizer cycle comprising the UV-C LEDs (11). For this, the device has a special arrangement of the ejection duct through which the flow is conducted (A), a micanita conductor that directs the air to the outside and a blade-type design that redirects the air back to the UV-C chamber.

Partial Polarity Reversal System:

The cell regeneration and breathing treatment equipment (100) comprises ionizers (12) used to change the electrical charge of the particles that are mostly positively charged and become negatively charged. The dual-channel, multi-cycle ejection system creates a recirculation of negatively charged particles so that between 10 and 20% of the air is again positively charged before ejection through the compression plates (6).

Thermal Sterilization System:

The cell regeneration and breathing treatment equipment (100) has a device that applies an electrical charge to the multifilament diffuser (2) made of stainless steel placed at the air outlet, so that it acts as a resistive unit at 300° C., sterilizing all the air before being ejected abroad. The split flow and recirculation system allows part of the air, e.g. 15/30%, to remain cold as it must return to the inside of the cell regeneration and breathing treatment equipment (100) for UV-C/Ionizer retreatment. If it were not for the split flow design and the configuration of the ejection duct directed by micanita (micanita is an electrical and thermal insulator), the hot air would recirculate inside the device creating a permanent increase in temperature that would make operation unviable.

Figure 3:
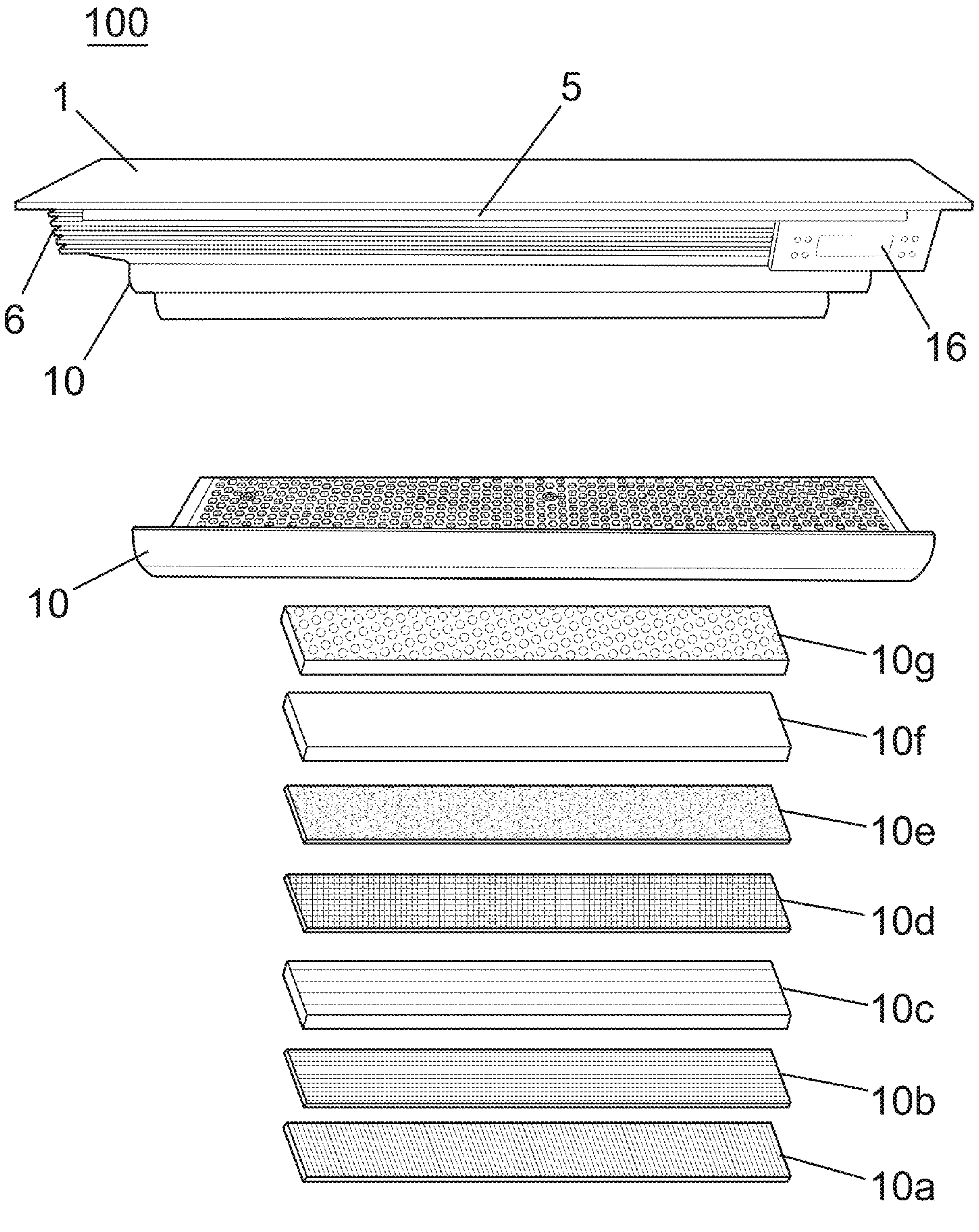
FIG. 3 shows the respiratory treatment equipment according to the present invention and the set of filters that comprise it.

The cell regeneration and breathing treatment equipment (100) works continuously (24 hours) and ultra-quietly to help rest and regenerate the body while sleeping. FIG. 3 shows a housing made of steel, as well as a front area that includes means for the ejection of air in laminar flow (6) and an LED display (16). The cell regeneration and breathing treatment equipment (100) launches a laminar flow of treated air that can be diverted by means for redirecting the laminar flow towards the face of the patient comprising a longitudinal deflector aluminum slat (5).

The cell regeneration and breathing treatment equipment (100) comprises a system of filters established in the structure (10):

To breathe the treated air, it is first passed through a washable pre-filter (10*a*) that removes the thickest particles to extend the life of the filter. The air is then passed through a first sterilizing antibacterial filter (10*b*). The air continues through a large, high-density HEPA 13 filter (10*c*), thus removing 99.9% of the suspended particles.

The air is filtered again through an activated carbon filter (10*d*) comprising capsules of activated carbon catalyzed with platinum, thus eliminating gases, odors and volatile organic compounds VOC, and Formaldehyde HVOC.

This highly purified air is passed through a photocatalytic filter (UV) (10*f*) that destroys bacteria, viruses, volatile organic compounds and nitrogen dioxide, thus achieving sterile air.

In case there could still be a particle smaller than 0.1 microns (0.0001 mm), the filter system comprises a double electrostimulating plasma filter that ionizes the air so that the particles are electrically charged by adhering to each other, creating larger particles, which will be filtered again.

Furthermore, the equipment (100) comprises a high-density silicon steel and/or silicon stabilizer (1) that absorbs all types of vibrations, together with the body of the equipment that, for this purpose, has been created 100% in steel and/or silicon, thus creating a high-density module that, when screwed under pressure against the equipment, provides rigidity, eliminates vibrations and allows the equipment to have a useful life of more than 35 years.

In addition, the equipment comprises a stainless steel filter (10*e*), in particular the stainless steel filter (10*e*) comprises a polished stainless steel grid which allows the equipment (100) to be used while the filters are removed for cleaning. The stainless steel filter (10*e*) has at least three functions:

1—Avoids access to moving parts of the equipment (100) to be able to use it without the changeable filter pack during the extraction and cleaning of said filter pack. This allows the air flow of the equipment (100) to be increased and the sound level to decrease. It can be very useful at times when the room is clean and a greater capacity for cooling or heating the environment is needed.

2. —The stainless steel filter (10*e*) allows coarse material filtering independent of the filtering carried out by the filter pack.

3. —The stainless steel filter (10*e*) generates reflections of ultraviolet rays that make them reach all the internal parts of the equipment, including the blades for the flow circulation, the carbon filter and other internal parts.

These reflections of ultraviolet light favor the internal sterilization of the entire equipment (100). This allows bacteria to never be sent to users.

Figure 4:
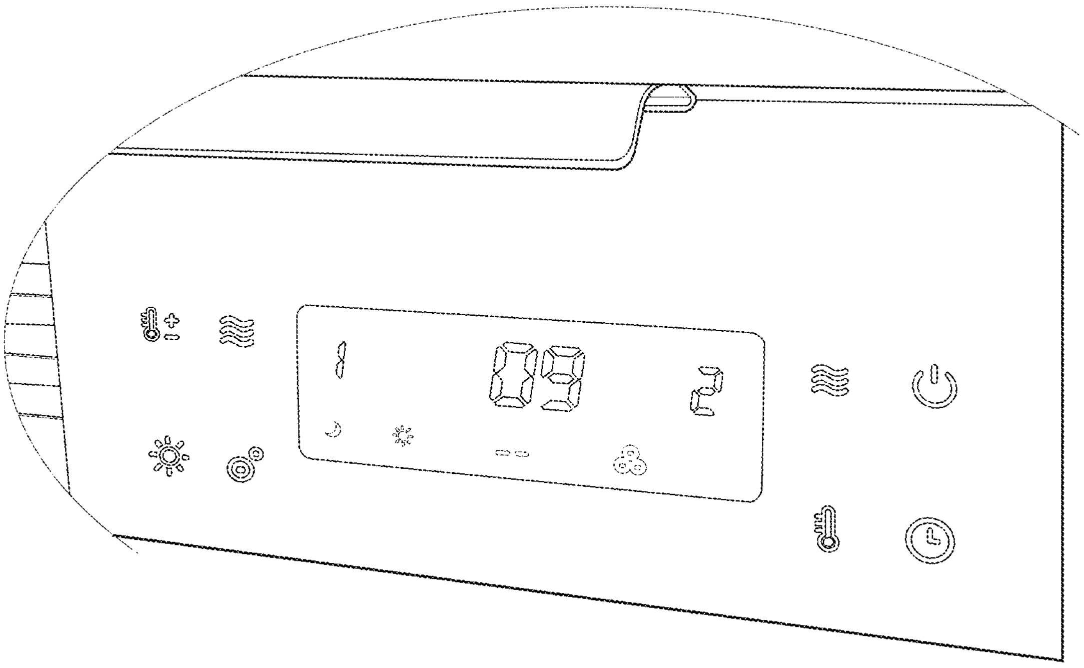
FIG. 4 shows the LED display of the cell regeneration and breathing treatment equipment according to the present invention.

FIG. 4 shows the high quality LED display (16) that permanently reports on the level of risk of contamination in blood (instantaneous level of nanoparticles), as well as the temperature of the room, the equipment systems in operation, a photosensitive control system to adapt to sleep mode, etc.

Figure 5:
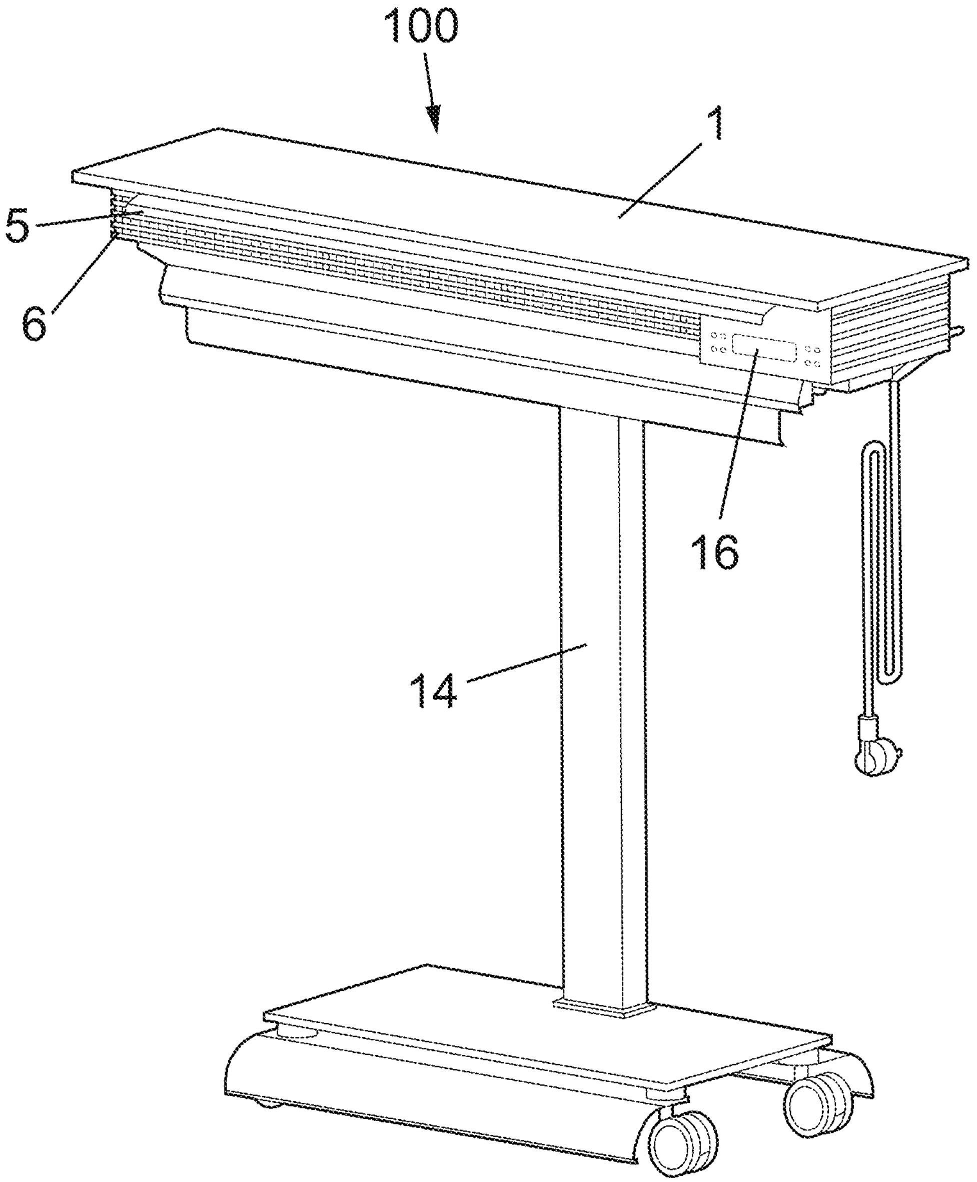
FIG. 5 shows the cell regeneration and breathing treatment equipment according to the present invention with a support system with wheels.

FIG. 5 shows the cell regeneration and breathing treatment equipment (100) according to the present invention with a support system with wheels (14) that allows it to be located in the optimal position so that the continuous laminar flow reaches the lungs of the patient while he/she sleeps, in particular at a height between 100 and 130 cm from the floor of the enclosure, and allows moving it from one room to another depending on who needs it more for health issues. In a preferred embodiment, the filter comprises anchoring means that allow the equipment (100) to be screwed to the wall, making the support system with wheels (14) unnecessary. The means for the ejection of air in laminar flow (6) and the longitudinal deflector aluminum slat (5) for redirecting the laminar flow towards the patient's face are also observed.

Figure 6:
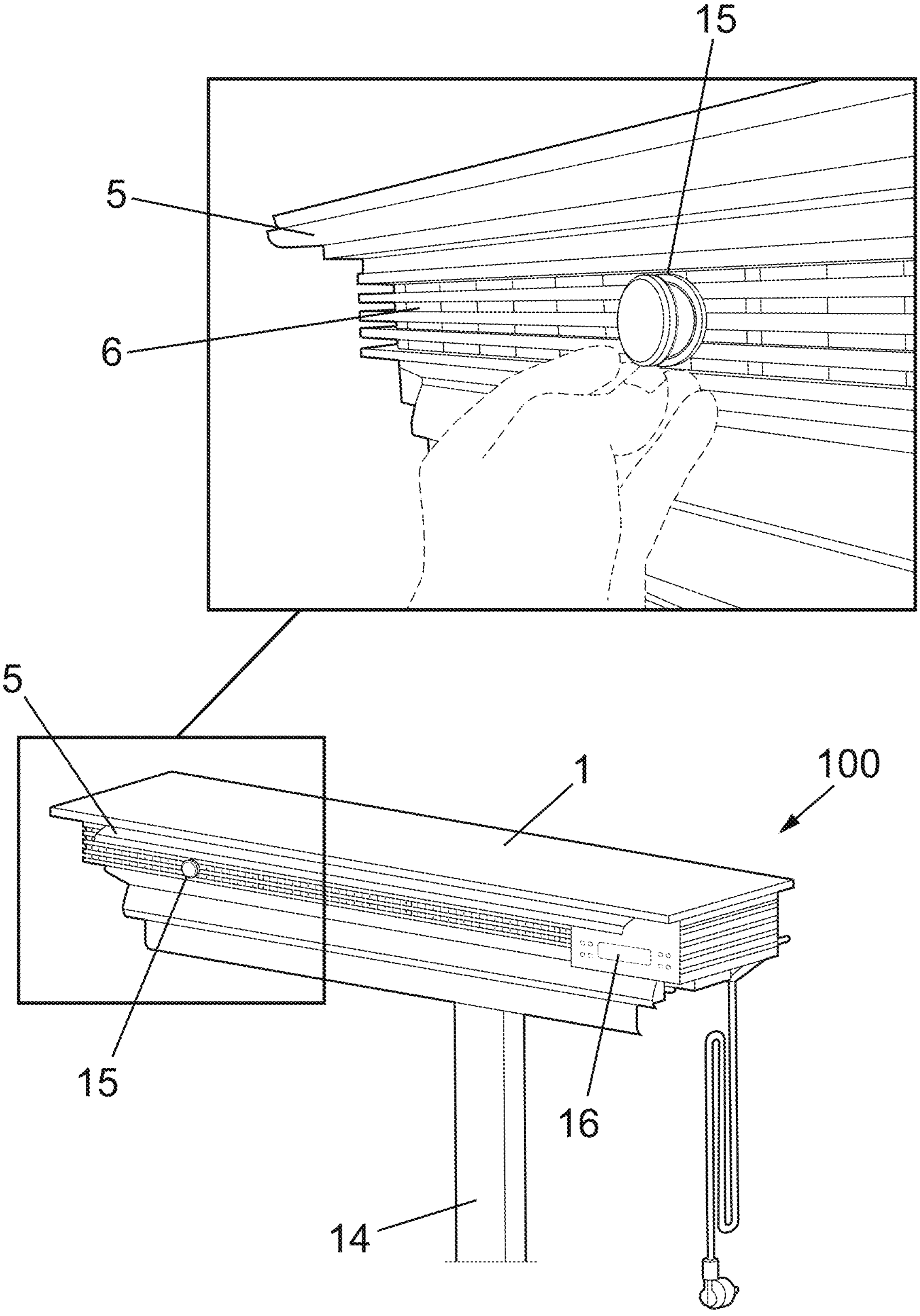
FIG. 6 shows the cell regeneration and breathing treatment equipment according to the present invention with a diffuser at the outlet of the air stream.

FIG. 6 shows the cell regeneration and breathing treatment equipment (100) according to the present invention with a diffuser (15) at the outlet of the air stream. The cell regeneration and breathing treatment equipment (100) incorporates a diffuser at the outlet of the treated air stream that allows the application of different substances that can be applied by inhalation. The diffuser (15) allows the incorporation of different treatments under medical prescription, such as bronchodilators or other types of substances that enhance the efficiency of breathing treatment and even allow intensive specific uses to treat crises of a different nature (asthmatic, allergic, etc.).

Figure 7:
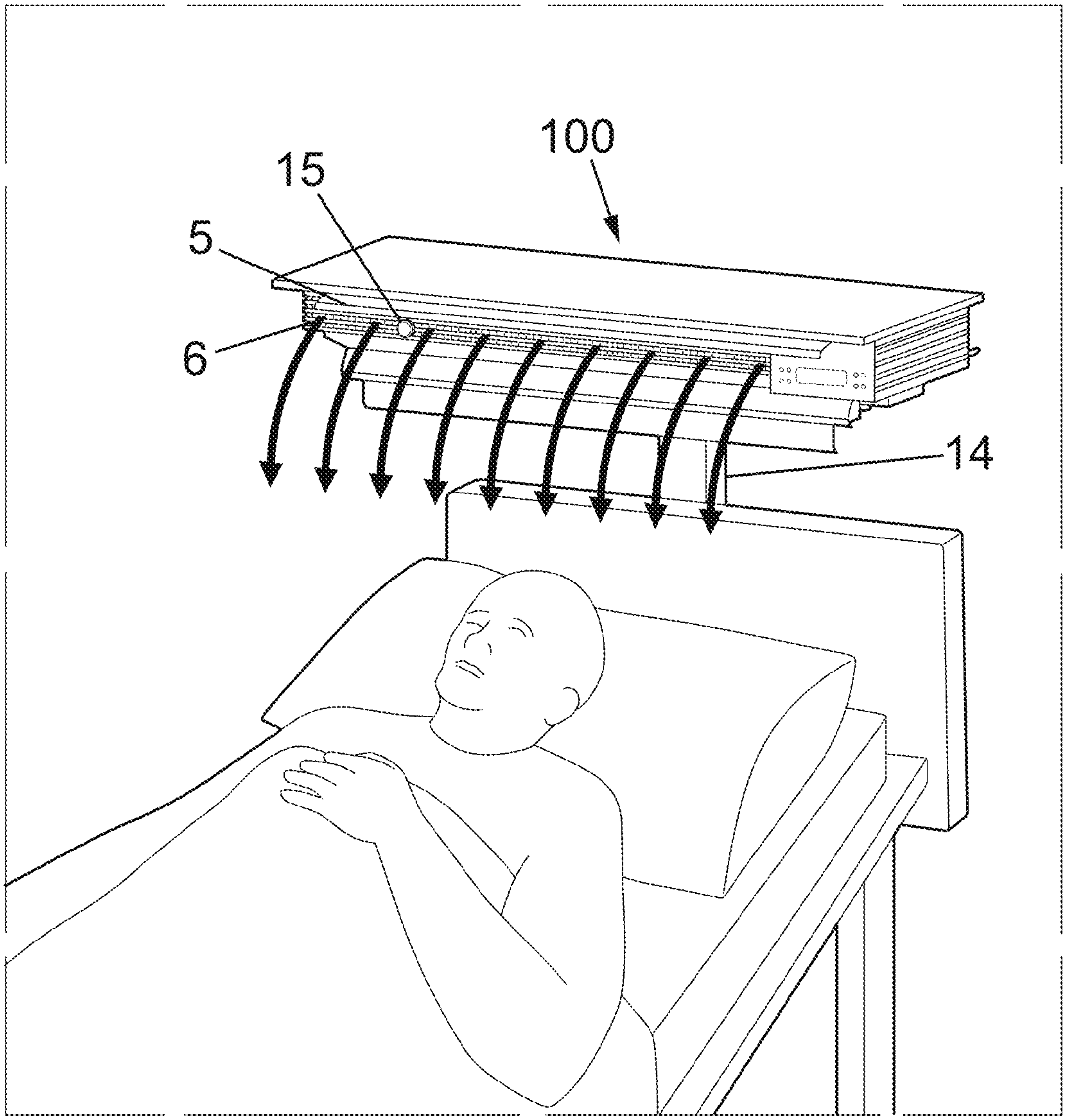
FIG. 7 shows the cell regeneration and breathing treatment equipment according to the present invention in operation with a patient.

FIG. 7 shows the cell regeneration and breathing treatment equipment (100) according to the present invention together with the diffuser (15) at the outlet of the air stream over the bed of a patient. The cell regeneration and breathing treatment equipment (100) comprises the support system (14) to establish the device at a height between 100 and 16 cm with respect to the floor of the enclosure that allows that the ejection of air in laminar flow through the means (6) be redirected through the aluminum deflector (65) towards the face of the patient and thus achieve optimal breathing.

Although reference has been made to specific embodiments of the invention, the breathing treatment units described in this document are susceptible to numerous variations and modifications, and all the mentioned features can be replaced by other technically equivalent, without departing from the scope of protection defined by claims.

The invention claimed is:

1. A respiratory treatment device for therapeutic use, the respiratory treatment device comprising:

a motorized air recirculation system;

filters for air purification;

an ultraviolet (UV) ray sterilizer;

a plasma electrostimulator;

an ejector of air in laminar flow;

a redirector of the laminar flow;

a stabilizer;

a stainless steel multifilament diffuser;

at least one UV-C light-emitting diode (LED); and a tangential fan configured to generate a centrifugal force to separate a first flow including particulate matter greater than 1 μm from a second flow including particulate matter smaller than 1 μm, wherein the motorized air recirculation system includes:

a motor configured to operate between 550 rpm-1200 rpm, and drive a system of tubular blades and a tubular steel integral recirculation system;

a device configured to apply an electrical charge to the stainless steel multifilament diffuser configured to function as a resistive thermal sterilizer configured to provide heat at 300° C.; and a tangential ventilation duct configured to: (i) convey the first flow outward from the device through the resistive thermal sterilizer; and (ii) facilitate recirculation of the second flow through the UV ray sterilizer and the plasma electrostimulator.

2. The respiratory treatment device according to claim 1, wherein the redirector includes an aluminum deflector.

3. The respiratory treatment device according to claim 1, further comprising a support system.

4. The respiratory treatment device according to claim 1, further comprising a wireless transmitter.

5. The respiratory treatment device according to claim 1, further comprising an LED display.

6. The respiratory treatment device according to claim 1, wherein the filters include a pre-filter, an antibacterial filter, a High Efficiency Particulate Air (HEPA) 13 filter, or a catalytic platinum activated carbon filter.

7. The respiratory treatment device according to claim 1, wherein the filters include a stainless steel filter.

8. The respiratory treatment device according to claim 1, wherein the stabilizer includes silicon.

9. The respiratory treatment device according to claim 1, further comprising an audible alarm.

10. The respiratory treatment device according to claim 1, further comprising a multilevel nanoparticle laser meter.

11. The respiratory treatment device according to claim 3, wherein the support system includes wheels.

12. The respiratory treatment device according to claim 8, wherein the stabilizer includes steel.

13. The respiratory treatment device according to claim 1, wherein the stabilizer includes steel.

* * * * *